(12) United States Patent  
Mozsáry et al.

(10) Patent No.: US 9,684,038 B2  
(45) Date of Patent: Jun. 20, 2017

(54) MAGNETIC FIELD SENSOR SYSTEM

(71) Applicant: ams AG, Unterpremstaetten (AT)

(72) Inventors: András Mozsáry, Unterpremstaetten (AT); Georg Roehrer, Lebring (AT)

(73) Assignee: AMS AG, Unterpremstaetten (AT)

( * ) Notice: Subject to any disclaimer, the term of this patent is extended or adjusted under 35 U.S.C. 154(b) by 115 days.

(21) Appl. No.: 14/775,646

(22) PCT Filed: Mar. 5, 2014

(86) PCT No.: PCT/EP2014/054272  
§ 371 (c)(1),  
(2) Date: Sep. 11, 2015

(87) PCT Pub. No.: WO2014/139848  
PCT Pub. Date: Sep. 18, 2014

(65) Prior Publication Data  
US 2016/0018475 A1 Jan. 21, 2016

(30) Foreign Application Priority Data  
Mar. 11, 2013 (EP) ..................................... 13158641

(51) Int. Cl.  
*G01R 33/025* (2006.01)  
*G01R 33/00* (2006.01)  
*G01R 33/10* (2006.01)  
*G01R 33/06* (2006.01)  
*G01R 35/00* (2006.01)  
(Continued)

(52) U.S. Cl.  
CPC ..... *G01R 33/0023* (2013.01); *G01R 33/0017* (2013.01); *G01R 33/0035* (2013.01);  
(Continued)

(58) Field of Classification Search  
CPC .......................... G01N 27/9086; G01R 35/005  
(Continued)

(56) References Cited

U.S. PATENT DOCUMENTS

| | | | |
|---|---|---|---|
| 4,596,950 A | 6/1986 | Lienhard et al. | |
| 5,521,501 A * | 5/1996 | Dettmann | G01R 33/096 324/207.12 |

(Continued)

FOREIGN PATENT DOCUMENTS

| | | |
|---|---|---|
| DE | 10 2011 017 096 A1 | 10/2012 |
| EP | 2624001 A1 | 8/2013 |

(Continued)

*Primary Examiner* — Reena Aurora  
(74) *Attorney, Agent, or Firm* — McDermott Will & Emery LLP

(57) ABSTRACT

A magnetic field sensor system has a plurality of magnetic field sensor elements, which each are configured to provide an individual sensor value, and of which a first portion is arranged in a first contiguous area and a second portion is arranged in a second contiguous area, and a coil wire arrangement with a first coil portion and at least a second coil portion being connected to the first coil portion, wherein the first coil portion is arranged close to the sensor elements of the first area and the second coil portion is arranged close to the sensor elements of the second area such that, if a predetermined current is applied to the coil wire arrangement, a first magnetic field component is generated at the first area and a second magnetic field component is generated at the second area being opposite to the first magnetic field component. The magnetic field sensor system is configured to produce a total sensor value that is based on a difference between the individual sensor values provided within the areas.

20 Claims, 11 Drawing Sheets

(51) Int. Cl.
  *G01N 27/90* (2006.01)
(52) U.S. Cl.
  CPC .............. *G01R 33/06* (2013.01); *G01R 33/10* (2013.01); *G01R 35/005* (2013.01); *G01N 27/9086* (2013.01)
(58) Field of Classification Search
  USPC ........................................................ 324/202
  See application file for complete search history.

(56) References Cited

U.S. PATENT DOCUMENTS

| | | | | |
|---|---|---|---|---|
| 6,529,114 B1 * | 3/2003 | Bohlinger | ............ | G01R 33/096 324/252 |
| 8,680,857 B2 * | 3/2014 | Phan Le | ................ | G01R 33/09 324/207.21 |
| 2007/0046287 A1 | 3/2007 | Vervaeke et al. | | |
| 2011/0031960 A1 | 2/2011 | Hohe et al. | | |
| 2012/0153942 A1 | 6/2012 | van Veldhoven et al. | | |
| 2014/0117983 A1 | 5/2014 | Roehrer | | |

FOREIGN PATENT DOCUMENTS

| | | |
|---|---|---|
| JP | 2000230969 A | 8/2000 |
| JP | 2008503778 A | 2/2008 |
| JP | 2010537207 A | 12/2010 |
| JP | 2013024871 A | 2/2013 |
| WO | 2008/017348 A2 | 2/2008 |
| WO | 2009/030361 A1 | 3/2009 |
| WO | 2012/140074 A1 | 10/2012 |
| WO | 2013/053534 A1 | 4/2013 |

* cited by examiner

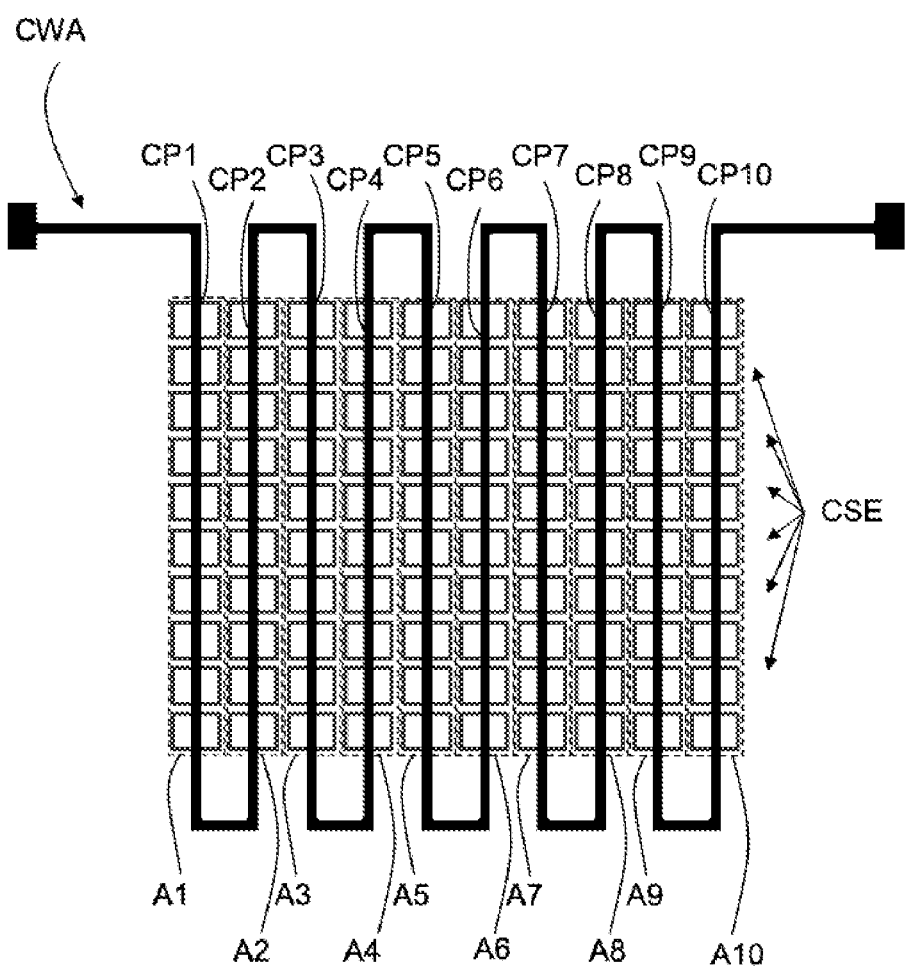

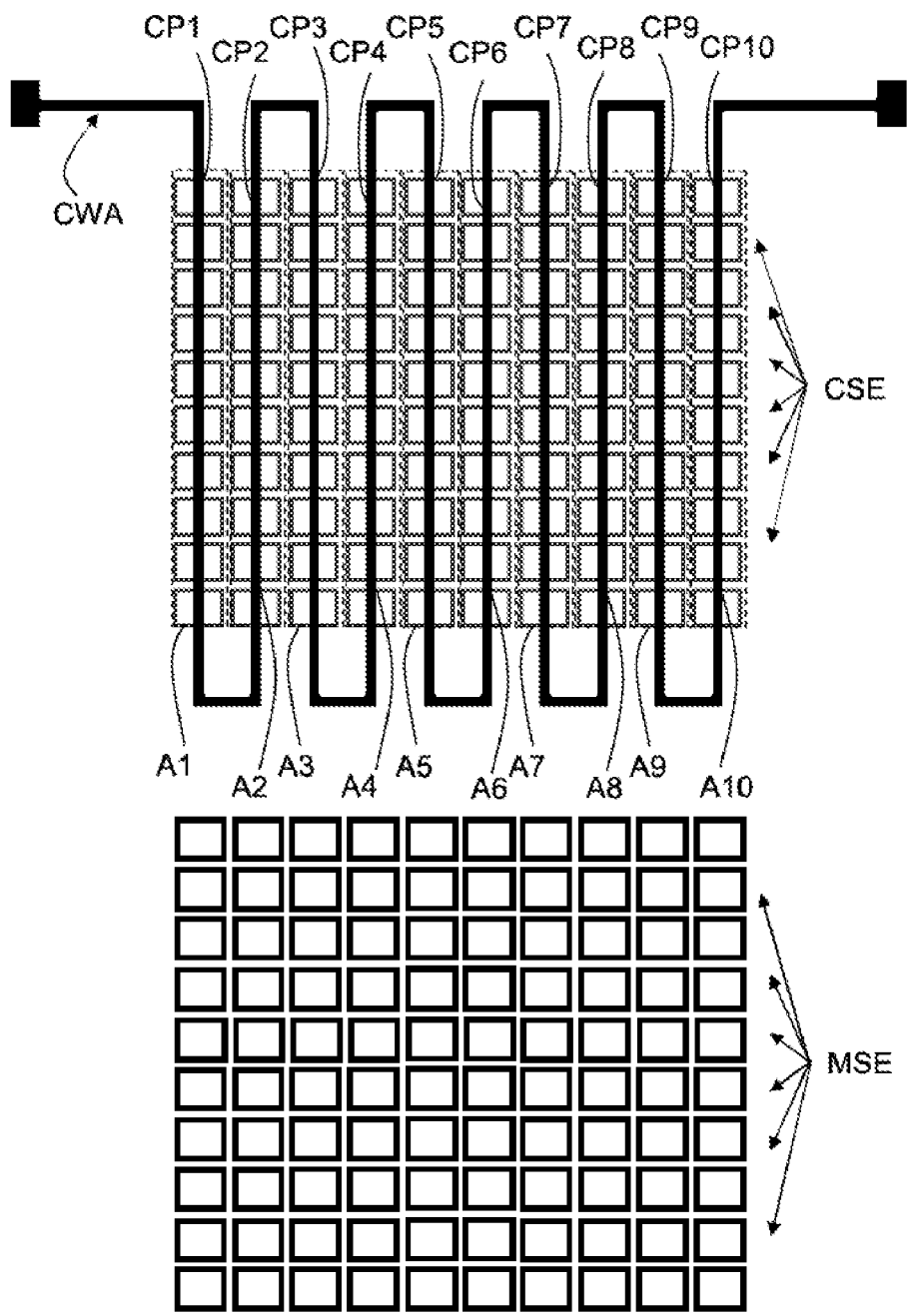

MAGNETIC FIELD SENSOR SYSTEM

FIELD OF THE INVENTION

The invention relates to a magnetic field sensor system, which particularly can be used for calibration purposes.

BACKGROUND OF THE INVENTION

In various applications, integrated coils are used with magnetic field sensors for generating magnetic fields for test or in situ calibration purposes. Such integrated coils are inter alia defined by a coil factor that determines the magnetic field generated per current applied to the coil. In particular, the field generated by the coil and sensed by a magnetic field sensor is based on the coil current multiplied by the coil factor, e.g. averaged over a sensor area of the magnetic field sensor. For a predetermined supply voltage the maximum coil current is obtained by dividing the supply voltage by an ohmic resistance of the coil. For large sensors the coil length becomes very long and hence the resistance of the coil is large. Thus, the maximum generated field achievable with a given supply voltage is limited.

A large sensor may be formed of a plurality of single sensor elements which can be connected electrically in different ways. In a calibration process, each of the sensor elements measures the magnetic field generated in the coil. In a conventional approach, a coil wire of the coil is arranged such that a homogeneous magnetic field is generated at the respective positions of each sensor element of the large sensor. This results in a higher length of the coil wire and thus a reduced effectiveness regarding calibration.

Document US 2011/0031960 shows a three-dimensional Hall sensor having asymmetrically distributed calibration wires provided at least over vertical Hall elements placed around a set of lateral Hall elements. A difference of different calibration field components is measured by averaging of the output signals of the partial sensors results.

SUMMARY OF THE INVENTION

An efficient concept for a magnetic field sensor system with a plurality of magnetic field sensor elements and a coil wire arrangement is provided.

For example, a magnetic field sensor system comprises a plurality of magnetic field sensor elements, each of which are configured to provide an individual sensor value in response to a magnetic field applied thereto. The sensor system further comprises a coil wire arrangement, to which a predetermined current can be applied in order to generate a magnetic field.

The efficient concept is based on the idea that the plurality of magnetic field sensor elements is divided into at least two portions, such that a first portion is arranged in a first contiguous area and a second portion of the magnetic field sensor elements is arranged in a second contiguous area. Furthermore, the coil wire arrangement comprises a first coil portion and at least a second coil portion being connected, in particular connected in series, to the first coil portion. The different coil portions are arranged such that the coil portions generate magnetic field components having mutually different orientations. For example, the first coil portion generates a positive magnetic field relative to a specific spatial dimension and the second coil portion generates a negative magnetic field with respect to that spatial dimension. The magnetic field generated by the first coil portion is sensed by the sensor elements of the first area, and the magnetic field generated by the second coil portion is sensed by the sensor elements of the second area. Preferably, the first portion is also interconnected in the first contiguous area and the second portion of the magnetic field sensor elements is also interconnected in the second contiguous area.

The resulting individual sensor values are combined together such that a difference is formed between the sensor values coming from the first area and the sensor values coming from the second area. Due to the opposite orientation of the magnetic field and the sensor values, respectively, a resulting total sensor value corresponds to the absolute sum of the individual sensor values.

According to the efficient concept, the at least two coil portions can be placed close to each other, i.e. anti-parallel, without the need for elongating the coil between the coil portions. Hence, the resistance of the coil wire arrangement can be optimized, resulting in a higher magnetic field based on the same supply voltage for the coil wire arrangement. The difference may be formed immediately by respective electrical interconnections of the magnetic field sensor elements, either separately in each area or in total for all of the magnetic field sensor elements. Also other ways to build the difference can be used. However, all of the individual sensor values preferably are provided concurrently, in particular during application of the supply voltage or a supply current to the coil wire arrangement.

According to an embodiment of a magnetic field sensor system, the first coil portion of the coil wire arrangement is arranged close to the sensor elements of the first area and the second coil portion is arranged close to the sensor elements of the second area such that, if a predetermined current is applied to the coil wire arrangement, a first magnetic field component is generated at the first area and a second magnetic field component is generated at the second area being opposite to the first magnetic field component. The magnetic field sensor system is configured to produce a total sensor value that is based on a difference between the individual sensor values provided within the first area and the individual sensor values provided within the second area. All the respective individual sensor values are provided concurrently.

The efficient concept can be used in a flexible way. For example, the plurality of magnetic field sensor elements are arranged in a total area having the same form or a similar form as an array of sensor elements to be calibrated. Such a sensor array may be placed in vicinity of the plurality of magnetic field sensor elements with the coil wire arrangement.

It is furthermore possible that the different areas of the magnetic field sensor system are arranged in an interleaved fashion, such that magnetic field sensor elements to be calibrated can be placed in between the different areas. Hence, a total area is formed both of magnetic field sensors used for calibrating and by magnetic field sensor elements used for measuring and to be calibrated.

As a still further option, the different areas formed by the plurality of magnetic field sensor elements are evaluated depending on the direction of the magnetic field component, such that for calibrating purposes a difference based on the individual sensor values is formed as described before, whereas for measuring purposes a sum based on the individual sensor values of all areas is formed.

According to various embodiments, each area is in the form of one or more straight columns or rows constructed of the respective portion of magnetic field sensor elements. For example, each area therefore has rectangular shape. For example, each column or row comprises four or more magnetic field sensor elements.

If an area is in the form of a single row or column, the magnetic field sensor elements of this area may be interconnected in a serial fashion or a parallel fashion or a combination of serial and parallel connections.

In some embodiments, at least one of the areas is in the form of at least two straight columns or rows. Such an area may be constructed of respective magnetic field sensor elements that are connected in a mesh having more than one dimension.

It should be noted that the different areas can have different sizes and different numbers of magnetic field sensor elements. However, it can be advantageous if all areas are constructed congenerously.

In various embodiments, the magnetic field sensor elements may be interconnected such that within their respective area the area has connections which allow operating the complete area like a single magnetic field sensor of a larger size. Additionally, or as an alternative, the single magnetic field sensor elements or the single areas may be interconnected such that one or more groups of areas can be operated like a single magnetic field sensor. For example, areas providing sensor values corresponding to a positive magnetic field component are connected together with fixed connections and areas providing a negative magnetic field component are electrically interconnected in a fixed fashion. This allows an easy forming of the above-described difference in order to produce the total sensor value. Additionally, if applicable, also a sum of the sensor values of the different areas can be easily produced.

Furthermore, also the whole plurality of magnetic field sensor elements may be interconnected in a mesh having more than one dimension in some implementations. For instance, all sensor elements providing sensor values corresponding to positive and negative magnetic field components are connected together with fixed connections, wherein connection terminals of the individual magnetic field sensor elements are chosen with their respective polarity. Hence, the difference, respectively the total sensor value can be taken at the external connections of the array of magnetic field sensor elements, which allows operating the complete array like a single magnetic field sensor of a larger size.

For example, the magnetic field sensor elements of at least two areas are interconnected in a mesh having more than one dimension. Such mesh may also be operated like a single magnetic field sensor of a larger size.

In the various embodiments of the magnetic field sensor system, each coil portion may be formed by a single wire or a parallel connection of at least two wires or by at least two wires guided in parallel. At least one wire of the respective coil portion is arranged close to each magnetic field sensor element of the respective area.

If an area is in the form of one or more straight columns or rows, as described above, at least one wire of the respective coil portion is arranged close to each column or row, respectively, of the respective area, in a straight or linear fashion.

In the various embodiments described above, the efficient concept was explained with respect to the definition of two areas being constructed of respective magnetic field sensor elements. However, it becomes even more efficient if the plurality of magnetic field sensor elements is divided into a greater number of areas with respective coil portions of the coil wire arrangement arranged close thereto. In such implementations, the individual sensor values of the further areas are evaluated similar to the first and the second area described above. In particular, an absolute value of the respective area is formed by adding or subtracting, respectively, a contribution of the area based on the individual sensor values and the positive or negative direction of the magnetic field component generated by the respective coil portion. Obviously, a sign of the total sensor value depends on direction of coil current, such that the sum, respectively absolute value, is either a positive or a negative value.

For example, a third portion of the plurality of magnetic field sensor elements is arranged in a third contiguous area. The coil wire arrangement comprises a third coil portion which connects serially after the second coil portion. In other words, the second coil portion is connected in series between the first coil portion and the third coil portion. The third coil portion is arranged close to the sensor elements of the third area such that, if the predetermined current is applied to the coil wire arrangement, a third magnetic field component is generated at the third area having the same orientation as the first magnetic field component. For example, when producing the total sensor value, the individual sensor values provided within the third area are treated like the individual sensor values provided within the first area, namely summed up with the same sign as for the first area.

In a further development, a fourth portion of the plurality of magnetic field sensor elements is arranged in a fourth contiguous area. The coil wire arrangement comprises a fourth coil portion that is attached serially to the third coil portion. In other words, the third coil portion is arranged between the second and the fourth coil portion. The fourth coil portion is arranged close to the sensor elements of the fourth area such that, if the predetermined current is applied to the coil wire arrangement, a fourth magnetic field component is generated at the fourth area having the same orientation as the second magnetic field component. In other words, the magnetic field components of the second and the fourth area have the opposite orientation to the magnetic field components of the first and the third area. As a consequence, the individual sensor values of the fourth area are treated like the individual sensor values of the second area during production of the total sensor value.

Preferably, the respective portions of the magnetic field sensor elements are also interconnected in their contiguous area.

For example, the total sensor value is based on a difference between a sum of the individual sensor values provided within the first and the third area and a sum of the individual sensor values provided within the second and the fourth area. The different areas, which preferably are in the form of one or more rows or columns, may be arranged in the order of their numbering. In such a configuration, the coil wire arrangement may be formed in a serpentine-like fashion such that one coil portion goes over the respective area in one direction and the following coil portion goes in the opposite direction over the following area, until all areas or all magnetic field sensor elements, respectively, are covered. This is also possible with an implementation with only two areas.

More generally speaking, two groups of areas can be formed, the first group for example comprising the odd-numbered areas, and the second group comprising the even-numbered areas. The difference is then formed between the individual sensor values of the first group and the individual sensor values of the second group, in order to produce the total sensor value.

In one specific implementation with at least four areas and respectively four coil portions, the coil wire arrangement may be in a snail-like fashion such that, for example, odd-numbered areas are arranged together and even-numbered areas are arranged together. The coil portions form a snail or spiral over the different areas.

For example, for a four-area configuration, the third and the fourth area are located between the first and the second area, wherein the third area is located next to the first area and the fourth area is located next to the second area. The coil portions are arranged in a spiral-like fashion close to the respective areas.

In an alternative implementation form with at least four areas, the coil portions form a bifilar winding. The bifilar winding is similar to the serpentine-like winding but at each position having a forward and a return path arranged close to each other. Accordingly, each two of the coil portions are guided in parallel close to two of the areas that are located neighbouring to each other. Preferably, the number of areas is even in order to implement the bifilar winding of the coil wire arrangement more easily.

In various embodiments, the different areas may be arranged spaced apart in order to reduce the influence of the coil portions to the respective neighbouring area.

In some embodiments, the magnetic field sensor system comprises two or more coil wire arrangements, which can be operated independent from each other. In particular, the different coil wire arrangements have independent supplies for the coil current or the voltage applied to the coil wire arrangement. All the coil wire arrangements can be constructed like the single coil wire arrangement with the different coil portions described above. In particular, the coil portions of the coil wire arrangements may be arranged close to the different areas in order to generate magnetic field components of opposite direction. The total sensor value can be generated in the same way as described above for the single coil wire arrangement.

More generally speaking, the single coil wire arrangement of the different embodiments described above may be split into two or more coil wire arrangements, each of which are supplied independently. The structure of any coil wires over the different areas, however, may be the same as that of the single coil wire arrangement.

By using two or more coil wire arrangements being supplied independently, for example supply voltage limitations can be overcome, e.g. by providing additional supply connections.

In various embodiments, the magnetic field sensor system is configured to apply a predetermined calibration current to the coil wire arrangement. In this case, the total sensor value produced during application of the calibration current corresponds to a calibration value. During operation of the magnetic field sensor system, a sign or flow direction of the current applied to the coil wire arrangement may be varied.

Such a calibration value may be used for calibration or measurement purposes, respectively. For example, the magnetic field sensor system comprises a further plurality of magnetic field sensor elements, each of which are configured to provide an individual sensor value in response to a magnetic field applied thereto and which are electrically interconnected. The magnetic field sensor system is configured to produce a measurement value on the basis of the individual sensor values of the further plurality of magnetic field sensor elements and the calibration value. If distinct magnetic field sensor elements are used for measurement purposes only, they may be interconnected similar to the interconnections of the various areas, but without forming a difference as described for the application with the coil. However, these sensor elements may be connected electrically in a mesh having more than one dimension.

In some embodiments, the magnetic field sensor system is configured to produce a measurement value that is based on a sum of the individual sensor values provided within the first area and the individual sensor values provided within the second area. Or, more generally speaking, the magnetic field sensor system may be configured to produce a measurement value that is based on a sum of the individual sensor values provided within the first group of areas and the individual sensor values provided within the second group of areas.

According to different implementations, the production of the total sensor value respectively calibration value and the production of the measurement value can be performed concurrently or non-concurrently, for instance in an alternating fashion.

Preferably, all the respective individual sensor values are provided concurrently, in particular for the concurrent production. This is also possible during application of a calibration current to the coil wire arrangement in case the signal contributions due to the magnetic field components generated by the coil wire arrangement cancel out each other.

Hence, each magnetic field sensor element serves a double purpose, namely for calibration purposes and measurement purposes. This reduces the size needed to implement the magnetic field sensor system.

Preferably, the measurement value produced by the magnetic field sensor system corresponds to an external magnetic field component. For example, the external magnetic field component is generated by an external permanent magnet or an external electromagnetic field. The external magnetic field can also be the magnetic field of the earth.

In the embodiments described above, the magnetic field sensor elements used for calibration and measurement may be integrated within a common semiconductor body. Hence, the magnetic field sensor system may be implemented within an integrated circuit.

For example all of the magnetic field sensor elements are of the same sensor type, which is selected from one of the following: a Hall sensor, a giant magnetoresistive, GMR, element, an anisotropic magnetoresistive, AMR, element and a tunnel magnetoresistive, TMR, element. The magnetic field sensor elements may be provided in or on a flat surface. The magnetic field sensor elements may be sensitive to magnetic field components being basically perpendicular to such a surface or being basically parallel to the surface.

Taking Hall sensors as an example, lateral Halls sensors may be used for the first case, whereas vertical Hall sensors may be used for the second case. Using magnetic field sensor elements being sensitive to components parallel to the surface may be advantageous because of an easy implementation of the coil wire arrangement. For example, a wire may be placed centered over the respective magnetic field sensor element in order to generate the magnetic field at the right position with the right orientation.

BRIEF DESCRIPTION OF THE DRAWINGS

The text below explains the invention in detail using exemplary embodiments with references to the drawings. Same references are used for same elements or circuit parts, or elements or circuit parts having a similar function in the various figures. Hence, the description of elements or circuit parts in one figure is not repeated in the following figures.

In the drawings:

FIG. 1 shows an embodiment of a magnetic field sensor system,

FIG. 2 shows a further embodiment of a magnetic field sensor system,

DETAILED DESCRIPTION

Figure 3A:
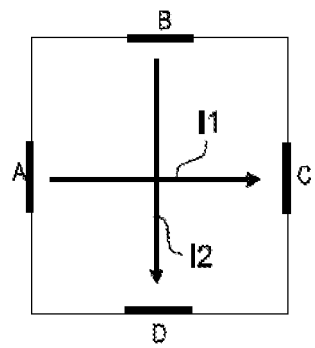
FIG. 3A shows an implementation of a lateral Hall sensor.

FIG. 1 shows an exemplary embodiment of a magnetic field sensor system that comprises a plurality of magnetic field sensor elements CSE. The sensor elements CSE are arranged in a 10×10 array, wherein lengths and widths of the array are chosen deliberately. In particular, also other sizes may be chosen, in particular with different sizes for width and length. Each magnetic field sensor element CSE is configured to provide an individual sensor value in response to a magnetic field applied thereto.

In this embodiment, the plurality of magnetic field sensor elements CSE is divided into ten separate contiguous areas A1 to A10. Hence, in each area A1 to A10, ten of the magnetic field sensor elements CSE are interconnected. In this embodiment, the spatial ordering of the areas A1 to A10 is according to their numbering.

The magnetic field sensor system further comprises a coil wire arrangement CWA, which, for example, is formed by a wire or a metal sheet placed over the array of magnetic field sensor elements CSE. The coil wire arrangement CWA comprises ten serially connected coil portions CP1 to CP10 with each coil portion CP1 to CP10 being arranged over one of the corresponding areas A1 to A10 containing the respective magnetic field sensor elements CSE.

In this embodiment, the coil wire arrangement CWA is formed in a serpentine-like fashion with each part of the serpentine being formed by one coil portion CP1 to CP10 that is arranged in a straight fashion over the row or column of magnetic field sensor elements CSE of the respective area. This has the effect that connections between the different coil portions can be kept as short as possible. Hence, a total resistance of the coil wire arrangement CWA can be kept low, in particular compared to conventional approaches.

Taking the embodiment of FIG. 1 and providing a predetermined DC current between the two ends of the coil wire arrangement CWA, it will become apparent to a skilled person that a magnetic field component generated by the first coil portion CP1 is of opposite direction to a magnetic field component generated by the second coil portion CP2. In general, the odd-numbered coil portions CP1, CP3, CP5, CP7, CP9 will generate a magnetic field component of one direction and the even-numbered coil portions CP2, CP4, CP6, CP8, CP10 will generate a magnetic field component of the opposite direction. Assuming that each of the magnetic field sensor elements CSE is basically sensitive to magnetic field of the same orientation, the magnetic field sensor elements CSE of the CSE of the odd-numbered areas A1, A3, A5, A9 will each provide an individual sensor value that has an opposite sign compared to the individual sensor values of the magnetic field sensor elements CSE of the even-numbered A2, A4, A6, A8, A10.

In order to achieve a result that is comparable to a homogeneous magnetic field over the total array of sensor elements CSE, the magnetic field sensor system is configured to produce a total sensor value that is based on a difference between the individual sensor values provided within the odd-numbered A1, A3, A5, A7, A9 and the individual sensor values provided within the even-numbered areas A2, A4, A6, A8, A10, wherein all the respective individual sensor values can be provided concurrently. Consequently, the total sensor value corresponds to a sum of the absolute values of the single areas A1 to A10. Obviously, a sign of the total sensor value depends on direction of coil current, such that the sum is either a positive or a negative value.

The total sensor value may be used as a calibration value for measurement purposes.

As the total resistance of the coil wire arrangement CWA can be achieved with a low value according to the embodiment of FIG. 1, a higher calibration current results when applying a predefined calibration voltage at the two ends of the coil wire arrangement CWA. As a consequence, the magnetic field intensity generated by the coil wire arrangement CWA is increased. As a result, the individual sensor values of the magnetic field sensor elements CSE have a higher significance due to the higher magnetic field intensity.

As mentioned in the beginning of the description of FIG. 1, the number of areas in coil portions can be chosen differently. For example, each number being equal or greater than 2 can be used to employ the described principle, namely forming a total sensor value based on the absolute values within each area, which in particular is performed by building respective differences.

More generally speaking, two groups of areas can be formed, the first group for example comprising the odd-numbered areas A1, A3, A5, A7, A9, and the second group comprising the even-numbered areas A2, A4, A6, A8, A10. The difference is then formed between the individual sensor values of the first group and the individual sensor values of the second group, in order to produce the total sensor value.

In various embodiments, the described principle can be used for a calibration of a magnetic field sensor before or during operation. For example, a further plurality of magnetic field sensor elements can be provided for the magnetic field sensor system, which are electrically interconnected. In such embodiments, the magnetic field sensor system is configured to produce a measurement value on the basis of the individual sensor values of the further plurality of magnetic field sensor elements and the calibration value. For example, the measurement value corresponds to an external magnetic field component.

FIG. 2 shows a specific implementation of such an embodiment, wherein the magnetic field sensor system comprises the arrangement shown in FIG. 1. As the magnetic field sensor elements of this arrangement of FIG. 1 are used for calibration purposes, they can also be called calibration sensor elements CSE. The magnetic field sensor system of FIG. 2 further comprises the further plurality of magnetic field sensor elements used for measuring purposes, which therefore can also be called measurement sensor elements MSE.

Preferably, the array of measurement sensor elements MSE has the same, or at least a similar size, to the array of calibration sensor elements CSE. This supports having the same or similar sensitivity of the resulting arrays, such that the calibration value generated by means of the calibration sensor element CSE has a high significance for the actual measurement with the measurement sensor elements MSE.

Each of the sensing elements CSE, MSE should be of the same sensor type and implementation. For example, the sensor elements MSE, CSE may be formed as Hall sensors, giant magnetoresistive, GMR, anisotropic magnetoresistive, AMR, elements, or tunnel magnetoresistive, TMR, elements, which per se are all well-known in the art. Such magnetic field sensor elements can be implemented such that they are sensitive to only magnetic field components of one direction in space. For example, the sensor elements, CSE, MSE, may be sensitive to magnetic field components being basically perpendicular to their surface, which may correspond to the surface of the array-like structure shown so far. Furthermore, the sensing elements may be sensitive to magnetic field components being parallel to said surface.

With respect to the implementations shown in FIG. 1 and FIG. 2 or in the following FIGS. 4 to 11, the magnetic field sensor elements CSE, MSE are sensitive to magnetic field components being basically parallel to the surface of the array and being perpendicular to the respective straight lines of the coil portions CP1 to CP10.

Although the different types of magnetic field elements can be used, Hall sensor elements are described briefly to better understand the underlying principle.

Figure 3B:
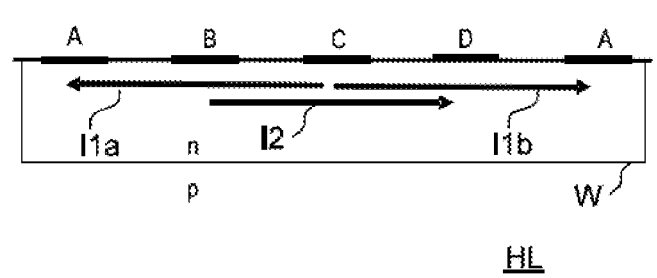
FIG. 3B shows an implementation of a vertical Hall sensor.

In FIG. 3A and FIG. 3B exemplary embodiments of Hall sensor elements are shown with possible directions of current flow during operation. Herein, FIG. 3A shows an embodiment of a lateral Hall sensor element, wherein in one operating phase of, for example, the spinning current technique, a current I1 flows form element terminal A to an element terminal C, while in another operating phase a current I2 flows from an element terminal B to an element terminal D. For example, centered on the sides of the Hall sensor element, which is shown as a square, electrical contacts are provided serving as element connections A, B, C, D. With such a lateral Hall sensor element, a magnetic field can be measured, which is perpendicular to the surface of the element shown as a square.

FIG. 3B illustrates an embodiment of a vertical Hall sensor element, for which for example an n-doped well W is provided within a p-doped semiconductor body HL. On the surface of the semiconductor body HL and the well W, respectively, contact pads for the element terminals A, B, C, D are provided, wherein the contact pad for the element terminal A is executed twice or symmetrically, respectively.

In analogy to the Hall sensor element shown in FIG. 3A, a current flows within the vertical Hall sensor element of FIG. 3B in a first operating phase from the element terminal C to the contact pads of the element terminal A, characterized by the flow arrows I1A, I1B. In a second operating phase, a current I2 flows from element terminal B to element terminal D in an analog way. With the Hall sensor element shown in FIG. 3B, a magnetic field being parallel to the surface of the semiconductor body HL or the well W can be measured. In particular, a measurement is performed of a magnetic field, which figuratively, runs vertical in the illustration of FIG. 3B.

Figure 4:
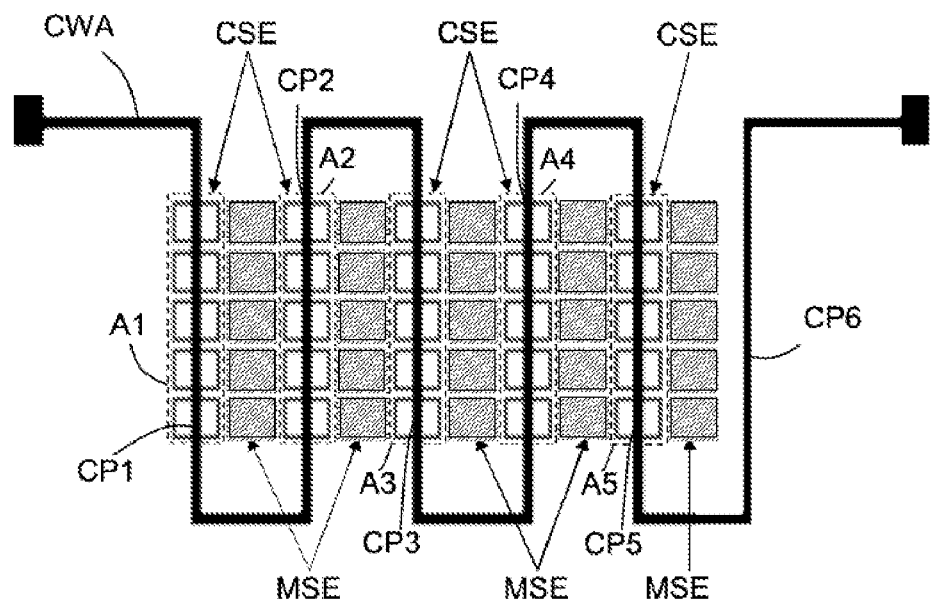
FIG. 4 to FIG. 12 show further embodiments of a magnetic field sensor system.

FIG. 4 shows a further embodiment of a magnetic field sensor system having a plurality of magnetic field sensor elements CSE, in particular calibration sensor elements, and the same number of measurement sensor elements. The embodiment of FIG. 4 is based on the same idea as FIG. 1 regarding the calibration process. To this end, the coil wire arrangement CWA has a serpentine-like shape. The magnetic field sensor system comprises five areas, A1, A2, A3, A4, A5 that have five calibration sensor elements CSE each, arranged in a single row. The areas A1 to A5 are arranged interleaved with a respective row of measurement sensor elements MSE arranged adjacent to each area A1 to A5.

Similar to the arrangement of FIG. 1, the odd-numbered areas A1, A3, A5 provide individual sensor values in response to a first magnetic field component produced by the coil portions CP1, CP3, CP5. The even-numbered areas A2, A4 provide individual sensor values corresponding to a magnetic field component of the opposite direction, produced by the corresponding even-numbered coil portions CP2 and CP4. Like in FIG. 4, a difference between the individual sensor values of the odd-numbered areas and the even-numbered areas is formed in order to have the absolute values. Due to the close arrangement of calibration sensor elements CSE and measurement sensor elements MSE, a good match between the sensor elements MSE, CSE can be achieved.

In the embodiment of FIG. 4, measurement is also possible during the times when a calibration current is applied to the coil wire arrangement CWA. To this end, the coil wire arrangement CWA comprises a sixth coil portion CP6 which is guided in parallel to the fifth coil portion CP5 without having sensor elements below. However, for the measuring sensor elements MSE on the right of the fifth area A5, the magnetic field components generated by the fifth coil portion CP5 cancels out the respective field components generated by the sixth coil portion CP6. It should be noted, however, that the coil portion CP6 can also be omitted, particularly if it is not intended to concurrently measure and calibrate. Furthermore, the coil portion CP6 may also be easily omitted, if the coil current is provided with alternating sign or flow direction over time.

Figure 5:
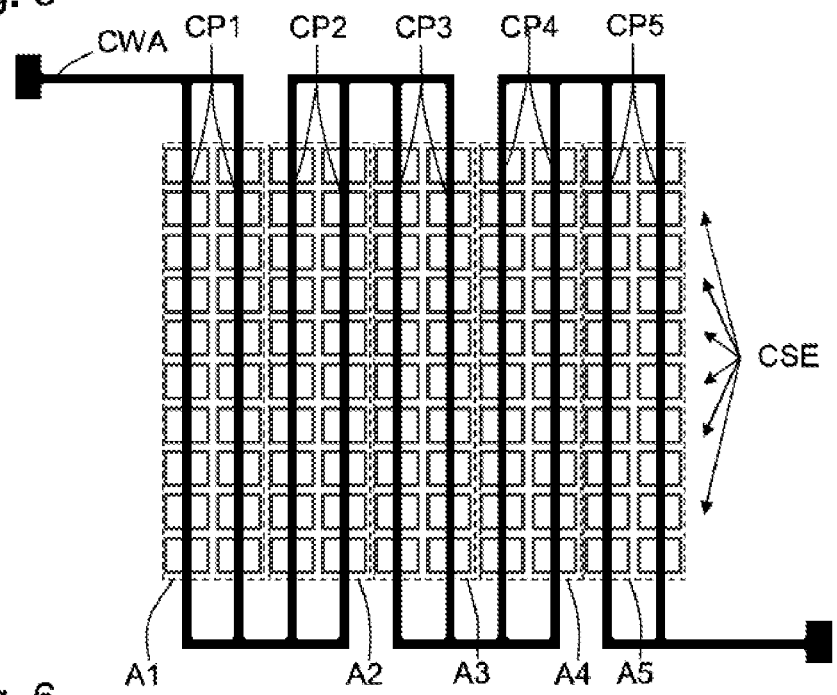

FIG. 5 shows a further embodiment of a magnetic field sensor system that is basically similar to that of FIG. 1. However, the calibration sensor elements CSE are divided into five areas A1, A2, A3, A4, A5 only, each of which are in the form of two straight rows constructed of the respective portion of the magnetic field sensor elements CSE.

Each of the corresponding coil portions CP1, CP2, CP3, CP4, CP5 is formed by a parallel connection of two wires, wherein in each case one wire is arranged close to or over each row of the respective area in a straight fashion. Due to the parallel connection of two wires in each coil portion CP1 to CP5, the resistance of the coil wire arrangement CWA is further reduced.

The evaluation of the concurrently measured individual sensor signals of the sensor elements CSE corresponds to the principle described before.

Figure 6:
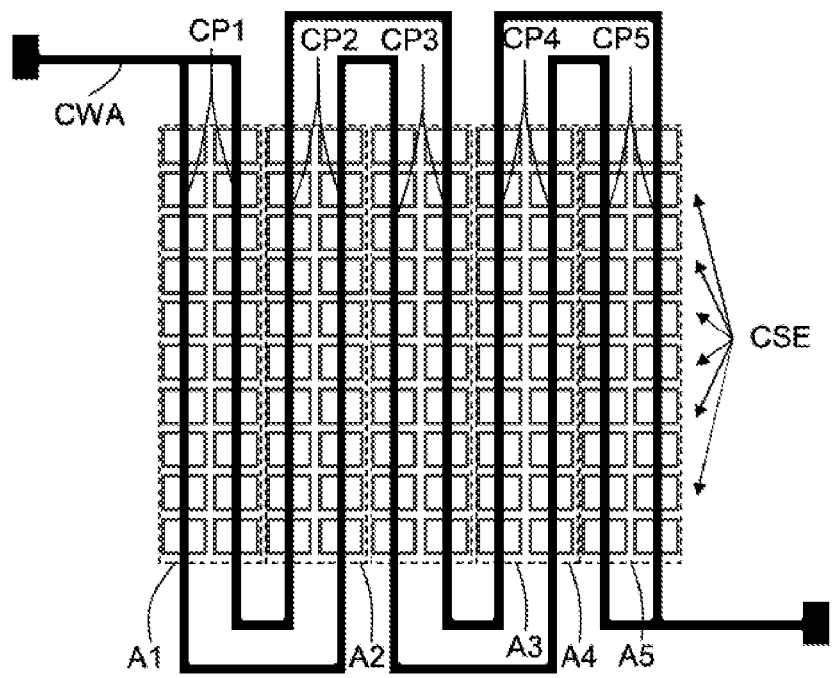

A similar embodiment of a magnetic field sensor system is shown in FIG. 6. In contrast to the embodiment of FIG. 5, the coil portions CP1 to CP5 do not consist of actual parallel connections of two wires, but of two wires which are guided in parallel close to or over the respective rows in each area. In each case, one wire of one area is serially connected to one wire of an adjacent area. From an electrical point of view, the coil wire arrangement CWA comprises two wires connected in parallel, wherein these parallel guided wires are arranged over the different areas A1 to A5 in a serpentine-like fashion. Regarding evaluation and determining of a calibration value, the same principle as applied, for example in FIG. 5, is used.

Figure 7A:
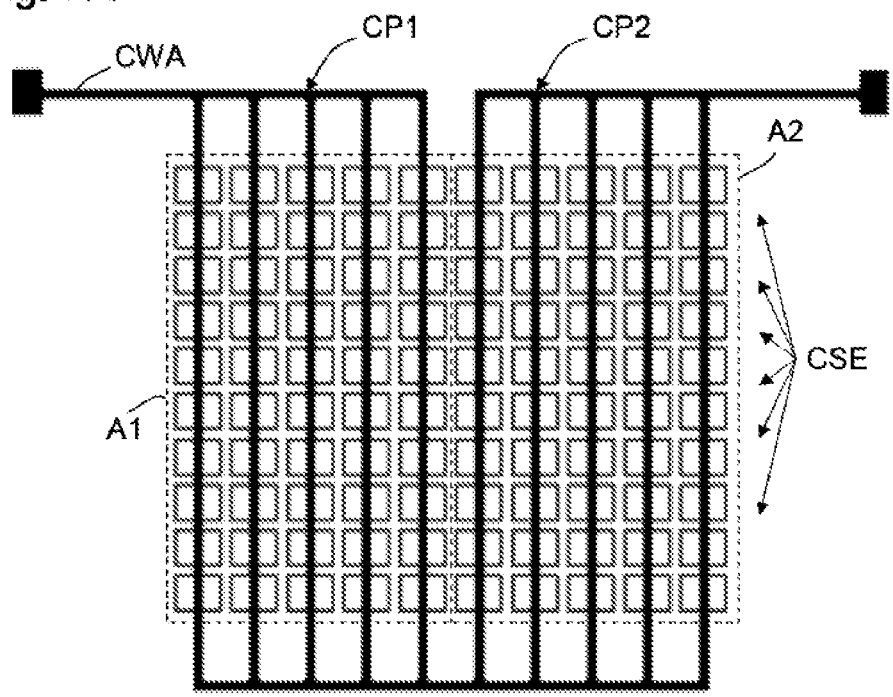
Figure 7B:
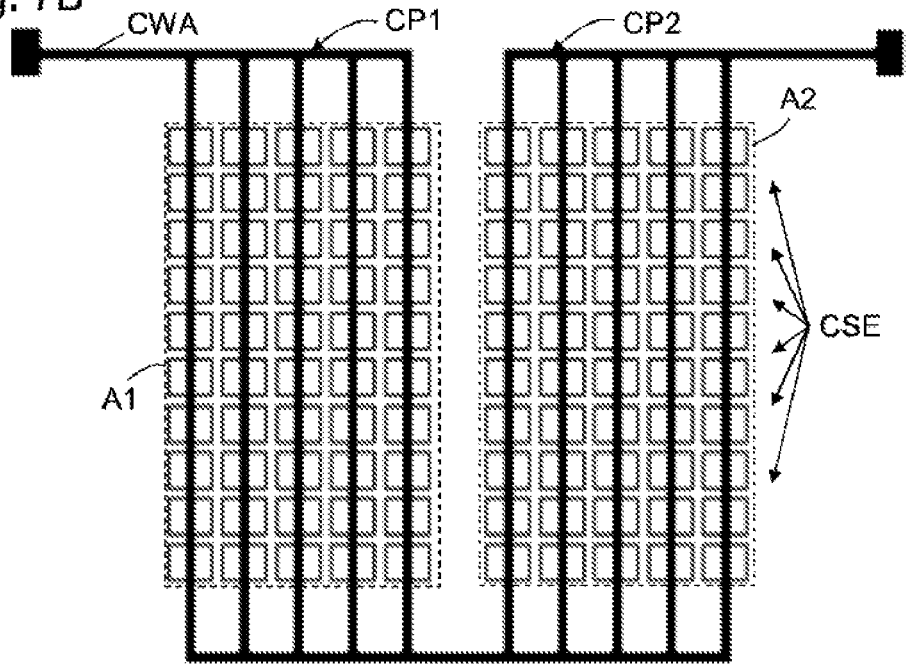

FIGS. 7A and 7B show further embodiments of the magnetic field sensor system which, like the previous examples, comprise a plurality of calibration sensor elements CSE and a coil wire arrangement CWA. In both FIGS. 7A and 7B the calibration sensor elements are divided into two areas A1, A2, each of which have a rectangular form and a size of 5×10 sensor elements. Accordingly, the coil wire arrangement CWA comprises two coil portions CP1, CP2, each of which are constructed from five parallel connected straight wires, wherein for each row of sensing elements CSE, one wire is arranged close to or over this row. If a calibration current is applied to the coil wire arrangement CWA, magnetic field components of different orientation are generated by means of the coil portion CP1 and CP2. According to the efficient concept, a difference is formed between individual sensor values generated within the first area A1 and the individual sensor values generated within the second area A2.

In FIG. 7A, the calibration sensor elements CSE are arranged with a regular spacing that is particularly continued between the edge rows of areas A1, A2. In contrast, in FIG. 7B the two areas A1, A2 are spaced apart. This reduces the mutual influence of the magnetic field generated by the respective other area. Hence, an even more precise calibration value can be achieved. In both embodiments of FIGS. 7A and 7B the coil resistance of the coil wire arrangement CWA can be kept low. Consequently, as for the other embodiments, a higher magnetic field can be generated.

Figure 8A:
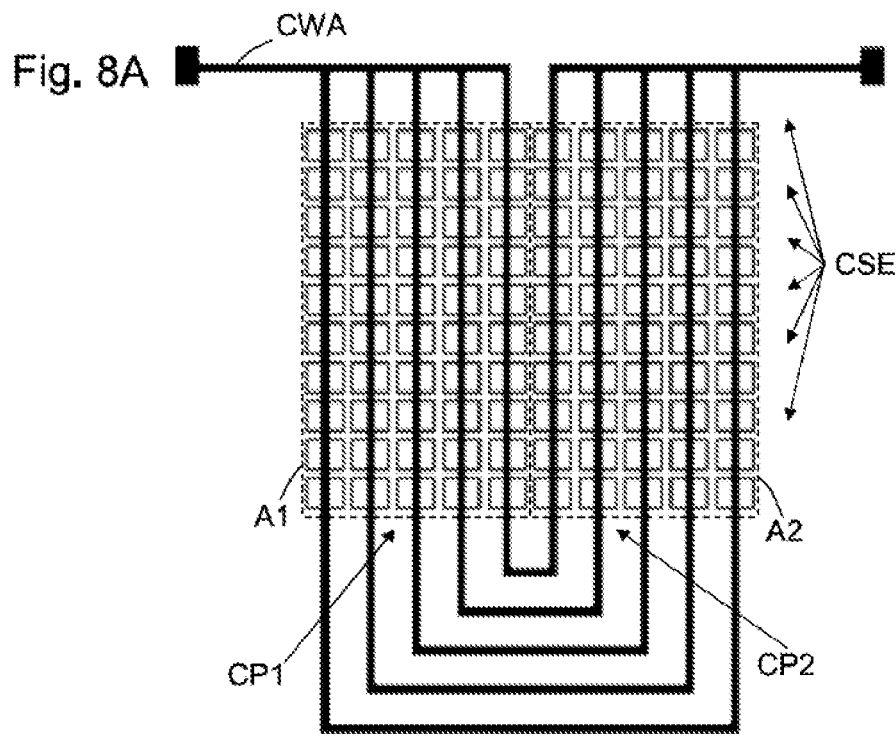
Figure 8B:
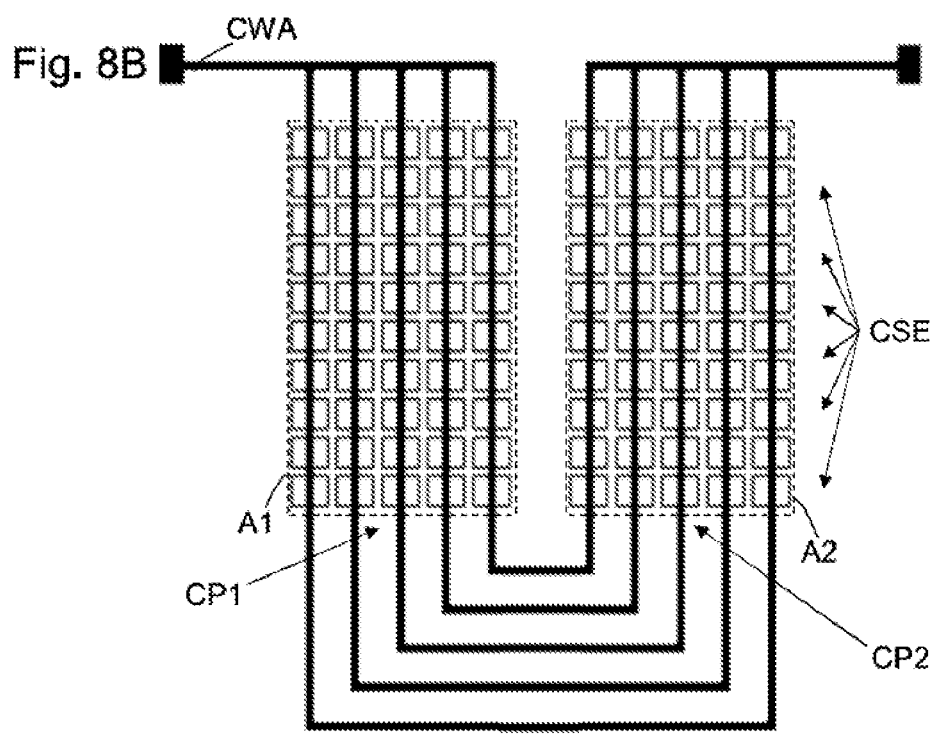

FIG. 8A and FIG. 8B show further embodiments of a magnetic field sensor system, which are similar to those of FIG. 7A and FIG. 7B. In particular, the plurality of calibration sensor elements CSE is divided into two areas A1, A2, and the coil wire arrangement CWA is divided into two coil portions CP1, CP2. However, like the transition from FIG. 5 to FIG. 6, the wires of the coil portions CP1, CP2 are not connected in parallel within each coil portion, but are solely guided in parallel over the respective rows of sensor elements CSE. In particular, each wire of the first coil portion CP1 is connected serially to exactly one of the wires of the second coil portion CP2.

As described for FIGS. 7A and 7B, the embodiment of FIG. 8A has a regular spacing for the calibration spacer elements CSE, whereas in the embodiment of FIG. 8B the two areas A1, A2 are spaced apart. Also here the influence of the magnetic field generated by one of the coil portions to the other area can be reduced.

It should be noted that in the embodiments shown in FIGS. 7A, 7B, 8A and 8B the size of the array of calibration sensor elements can be varied, for example depending on the size of an array of measuring sensor elements MSE, not shown here. Preferably, the number of parallel connected or parallel guided wires of each coil portion CP1, CP2 is the same. Additionally, in further embodiments, the number of wires in each coil portion could be increased in order to be different from the number of rows. For example, for each row there may be two wires guided in parallel close to the sensor elements CSE of this row. Hence, a condensed arrangement of wires within the coil wire arrangement CWA can be used. This can further increase the magnetic field to be sensed by the sensor elements CSE during application of a calibration current to the coil wire arrangement CWA.

Figure 9A:
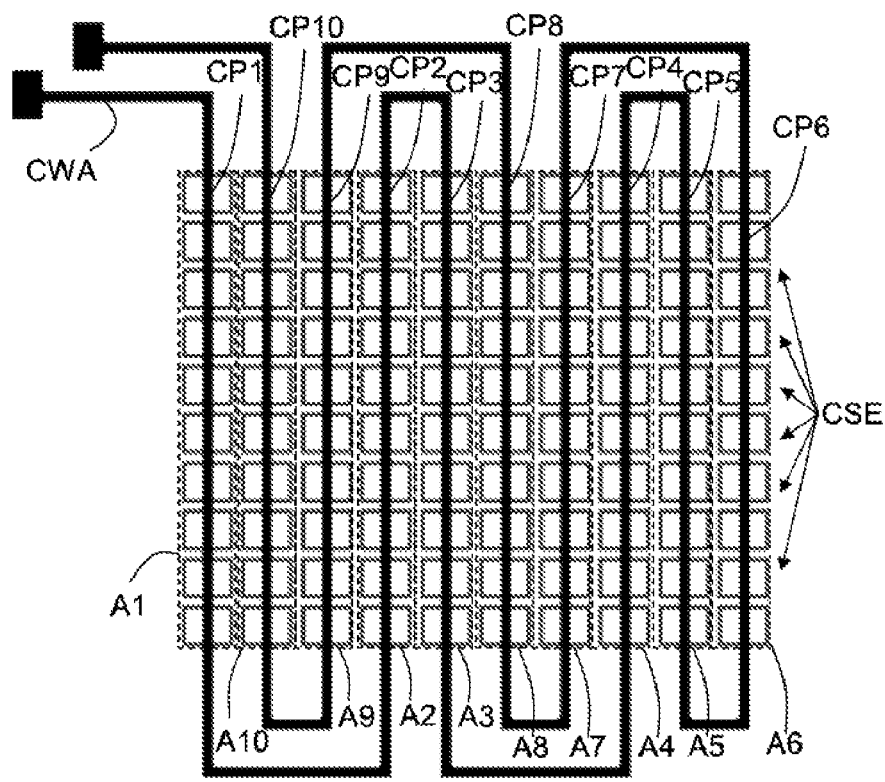
Figure 9B:
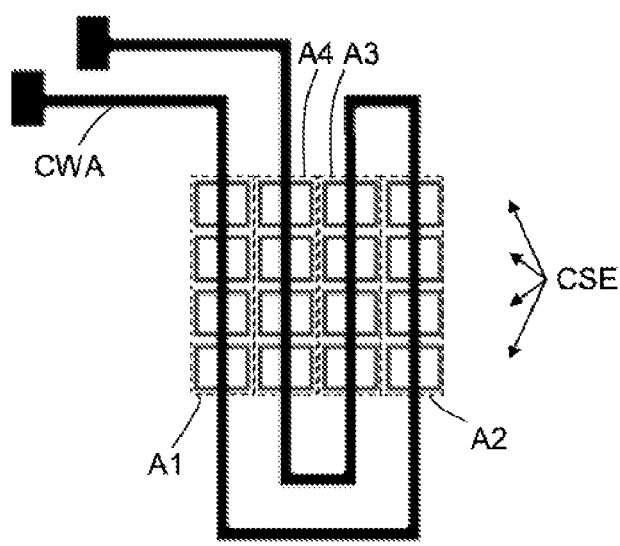

FIGS. 9A and 9B show embodiments of a magnetic field sensor system, in which the coil wire arrangement CWA is in the form of a bifilar winding. In FIG. 9A a 10×10 array of calibration sensor elements is provided, which are divided into ten areas A1 to A10, each formed by a single row of sensor elements CSE. In contrast to the previous embodiments, in particular with respect to the embodiment of FIG. 1, the ordering of the different areas A1 to A10 is varied. Having in mind a current direction of the calibration current, the respective coil portions CP1 to CP10 are arranged such that one coil portion in the forward direction is arranged in parallel to a coil portion in the reverse direction, thus forming the bifilar structure of the coil wire arrangement CWA. The parallel guided forward and reverse portions wind from the left side to the right side of the array.

The bifilar arrangement reduces the magnetic field to be sensed outside of the system, as the respective field components cancel out each other with increasing distance from the coil wire arrangement CWA. However, as in the embodiment of FIG. 1, the sensor elements CSE of the group of the odd-numbered areas A2, A3, A5, A7 and A9 sense a magnetic field component of one direction, whereas the calibration sensor element CSE of the group of the even-numbered areas A2, A4, A6 and A8 and A10 sense the magnetic field component of the opposite direction. As explained before, a calibration sensor value is formed by the magnetic field sensor system based on a difference between the individual sensor values from the odd-numbered areas and the individual sensor values of the even-numbered areas.

FIG. 9B shows an embodiment of a magnetic field sensor system with a bifilar winded coil wire arrangement CWA of a reduced size, namely a 4×4 array of calibration sensor elements CSE with respectively four areas, A2, A2, A3, A4 and four coil portions CP1, CP2, CP3, CP4. The same principles as explained for FIG. 9A apply here.

Figure 10A:
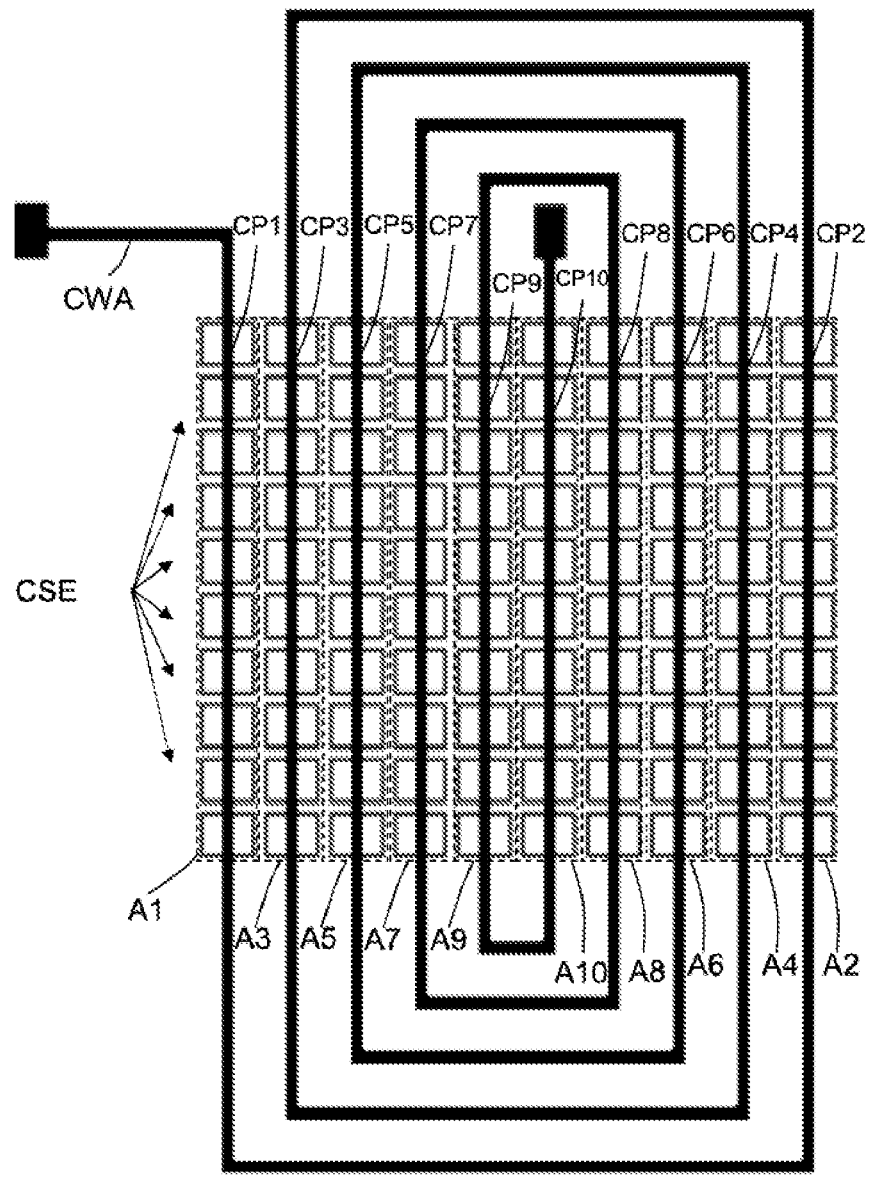
Figure 10B:
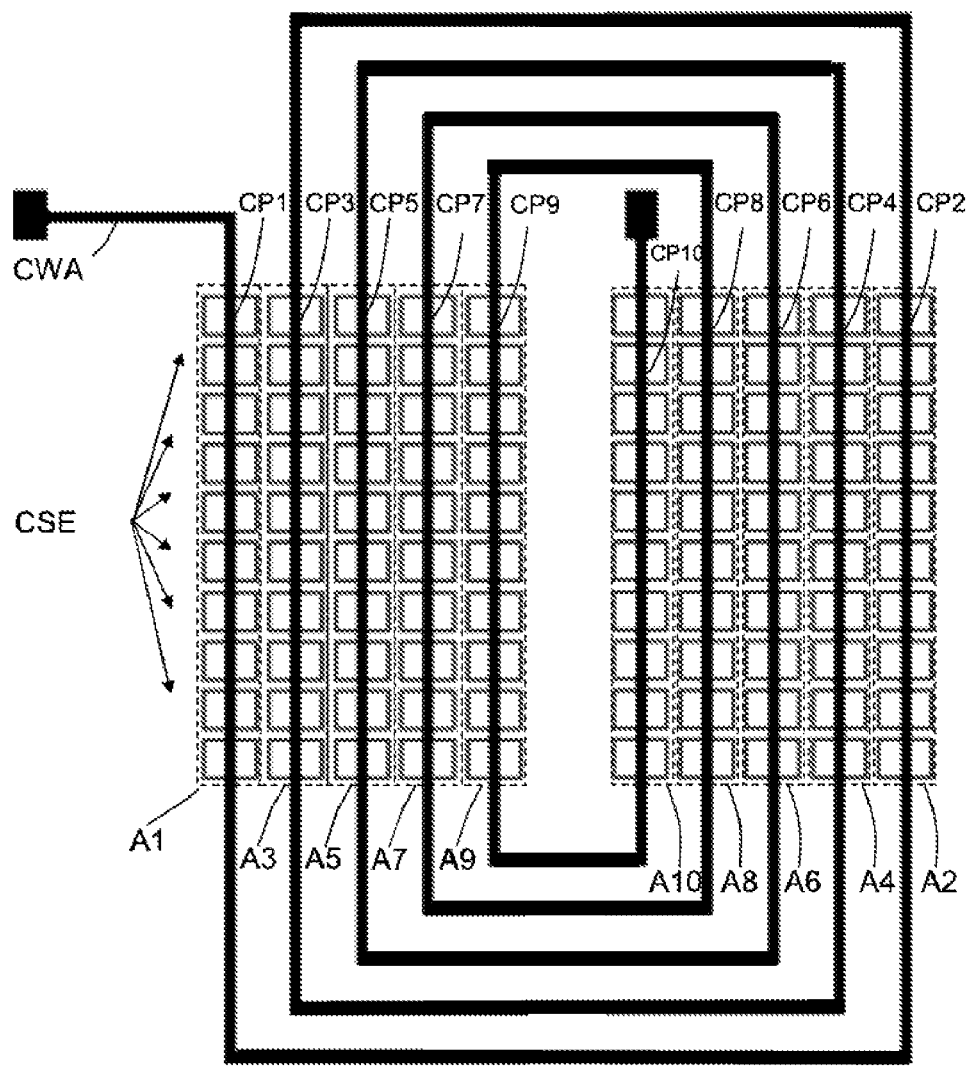

FIGS. 10A and 10B show further embodiments of a magnetic field sensor system, in which the coil wire arrangement CWA has coil portions CP1 to CP10 being arranged in a spiral-like fashion close to the respective areas A1 to A10. In the embodiments of FIGS. 10A and 10B, the spiral winds from the outer areas A1, A2 to the inner areas A9, A10. Accordingly, in the left half of the array of calibration sensor elements CSE, the odd-numbered areas A1, A3, A5, A7, A9 are located, whereas in the right half, the even-numbered areas A2, A4, A6, A8, A10 are located. Hence, if a DC current is applied as a calibration current to the coil wire arrangement CWA, in each half the current flows in the same direction, thus generating a magnetic field of the same orientation. For respective calibration sensor elements CSE, this is similar to the embodiments shown in FIGS. 7A, 7B, 8A and 8B, despite the differing coil resistance. However, evaluation of the individual sensor signals in order to produce the total calibration value is the same as described for FIGS. 7A, 7B, 8A and 8B.

With reference to the differences between FIGS. 7A and 7B or between FIGS. 8A and 8B, respectively, the embodiment of FIG. 10B differs from the embodiment of FIG. 10A that the two halves having the odd-numbered arrays A1, A3, A5, A7, A9, and the even-numbered arrays A2, A4, A6, A8, A10, are arranged spaced apart, thus reducing the mutual influence of the magnetic fields generated.

Figure 11:
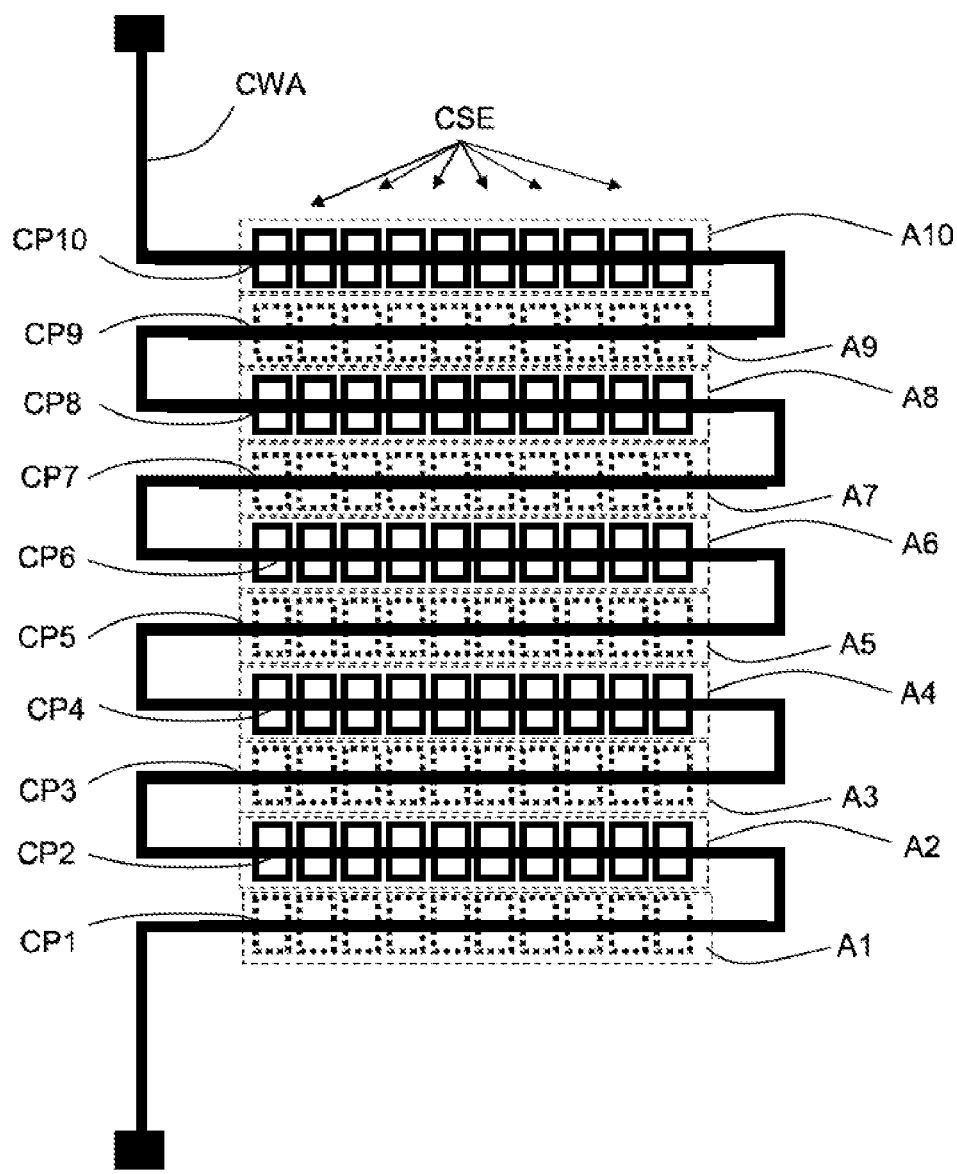

FIG. 11 shows a further embodiment of a magnetic field sensor system, which regarding the placement of the calibration sensor elements CSE and the coil wire arrangement CWA, is based on the embodiment of FIG. 1. However, in the embodiment of FIG. 11, two groups of sensor elements, respectively areas, are formed, namely the group of odd-numbered areas A1, A3, A5, A7, A9, in which the sensor elements CSE are marked with dashed lines, and the group of even-numbered areas A2, A4, A6, A8, A10, in which the sensor elements CSE are marked with solid lines.

According to this embodiment, the magnetic field sensor system is configured to produce a first value based on a combination of the individual sensor values of the first group and to produce a second value based on a combination of the individual sensor values of the second group. With respect to the previous explanations, a calibration value can be achieved by forming a difference between the first value and the second value, thus achieving, so to say, an absolute value of the magnetic fields generated, if a calibration current is applied to the coil wire arrangement CWA.

In addition, the magnetic field sensor arrangement is configured to produce a measurement value based on a sum of the first and the second value, thus corresponding to an external magnetic field. This is possible both during application of the calibration current and without the calibration current applied, as the respective magnetic field components cancel out each other due to the respective different orientations. This works best if positive and negative contributions are distributed equally. According to different implementations, the production of the total sensor value respectively calibration value and the production of the measurement value can be performed concurrently or non-concurrently, for instance in an alternating fashion. In particular for the concurrent production, the same individual sensor values are used for both the measurement value and the total sensor value respectively calibration value.

The arrangement shown in FIG. 11 has the advantage that the magnetic field sensor elements CSE can be used both for calibration and measuring purposes. Hence, no additional magnetic field sensor elements for measuring an external field are necessary.

Figure 12:
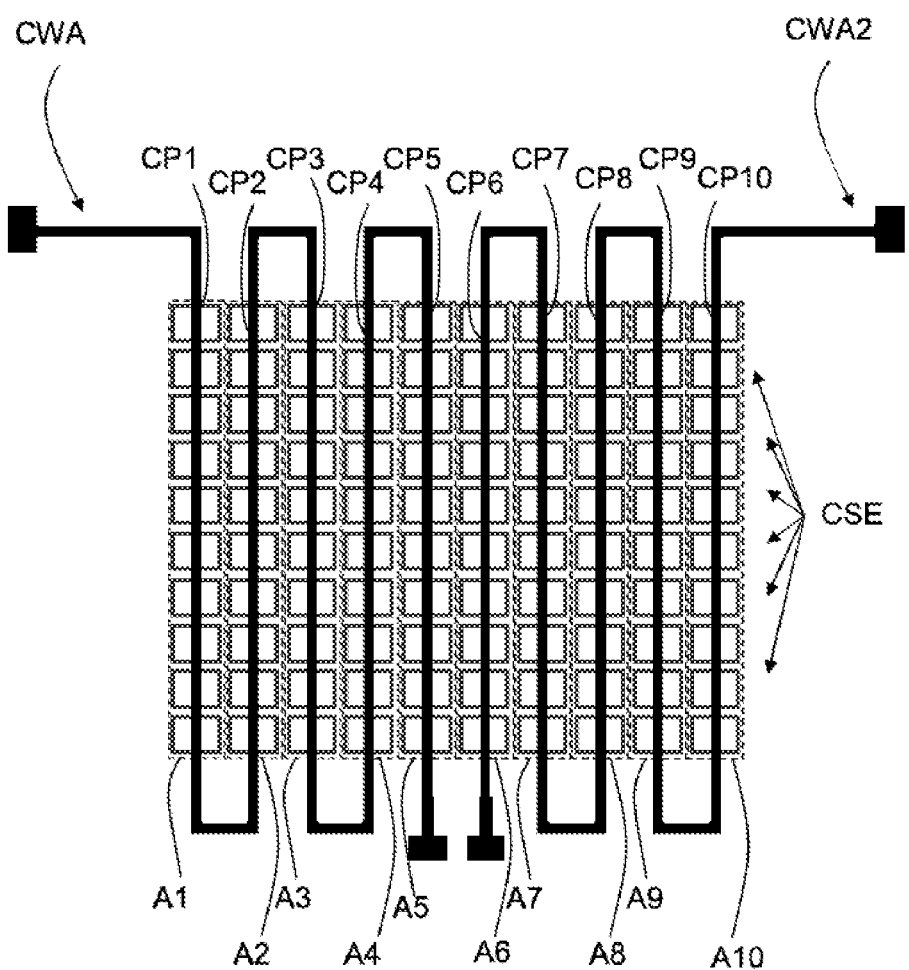

FIG. 12 shows a further embodiment of a magnetic field sensor system, which is based on the embodiment of FIG. 1. In particular, the same number of magnetic field sensor elements CSE and the same order of areas A1, . . . , A10 is provided. As a difference to the embodiment of FIG. 1, the embodiment of FIG. 12 comprises two coil wire arrangements CWA, CWA2. The first coil wire arrangement CWA comprises the coil portions CP1 to CP5 arranged over areas A1 to A5, whereas the second coil wire arrangement CWA2 comprises the coil portions CP6 to CP10 arranged over areas A6 to A10. The two coil wire arrangements CWA, CWA2 can be supplied independent from each other.

Compared to the embodiment of FIG. 1, the coil wire arrangement of FIG. 1 is split up into two coil wire arrangements in FIG. 12. For instance, supply voltage limitations can be overcome by this measure. In further embodiments not shown here, an even greater number of coil wire arrangements can be provided with the magnetic field sensor system.

During operation of the magnetic field sensor system, the evaluation of the individual sensor values of the magnetic field sensor elements CSE corresponds to that of the embodiment of FIG. 1.

In the above-described embodiments various examples are shown which implement the principle of the effective concept. In particular, the coil wire arrangement CWA in each case is formed and arranged such that a magnetic field is generated having different orientations at different coil portions. Furthermore, an absolute value of the resulting individual sensor values is formed, in particular by forming a difference of the individual sensor values.

The embodiments described above can all be used with or for an additional array of magnetic field sensor elements, in particular measurement sensor elements of the same or a similar size and number of elements, as for example shown in FIG. 2.

The effective concept can be used with various magnetic field sensor elements being sensitive to magnetic field components in one of different possible spatial orientations. In particular, magnetic field sensor elements can be used that are sensitive to components perpendicular to their surface or that are sensitive to magnetic field components being parallel to their surface. This was demonstrated in FIG. 3A and FIG. 3B as an example for lateral and vertical Hall sensors. The coil portions can be arranged such that the magnetic field component generated can be sensed by the respective used magnetic field sensor element.

The magnetic field sensor elements preferably are interconnected within their areas in order to reduce the number of connection wires from the sensor elements to an evaluation circuit. For example in areas having one row or one column, the sensor elements can be connected serially or in parallel within the area or a combination thereof. Such interconnections are, for example, described in international patent application publication WO 2012/140074 A1, which is incorporated herein by reference in its entirety.

In areas being constructed of two or more rows, or for at least two areas, the magnetic field sensor elements can also be connected in a mesh-like connection, in particular within a mesh having more than one dimension. That means that not each single connection of a sensor element is contacted from the outside, but for some of the sensor elements only internal connections between these sensor elements exist. This is described in more detail within international patent application PCT/EP2012/066697, which is incorporated herein in its entirety.

The difference to be formed between the different areas can be produced by separately evaluating the individual sensor values of the respective areas having the same orientation. This may, for example, be applicable to the embodiment shown in FIG. 11. However, the difference can also be formed by respective electrical connections taking into account a polarity of a single sensor output. Such implementations are, for example, described in European patent application EP 121543493, which is incorporated herein in its entirety.

The invention claimed is:

1. A magnetic field sensor system, comprising
a plurality of magnetic field sensor elements, which each are configured to provide an individual sensor value in response to a magnetic field applied thereto, and of which a first portion is arranged in a first contiguous area, a second portion is arranged in a second contiguous area and a third portion is arranged in a third contiguous area, wherein the first, the second and the third area are distinct from each other; and
a coil wire arrangement comprising a first coil portion, a second coil portion and at least a third coil portion being connected in series, such that the second coil portion is connected in series between the first coil portion and the third coil portion, wherein the first coil portion is arranged close to the sensor elements of the first area, the second coil portion is arranged close to the sensor elements of the second area and the third coil portion is arranged close to the sensor elements of the third area such that, if a predetermined current is applied to the coil wire arrangement, a first magnetic field component is generated at the first area, a second magnetic field component is generated at the second area being opposite to the first magnetic field component and a third magnetic field component is generated at the third area having the same orientation as the first magnetic field component;
wherein the magnetic field sensor system is configured to produce a total sensor value that is based on a difference between a sum of the individual sensor values provided within the first and the third area and a sum of the individual sensor values provided within the second area.

2. The system according to claim 1,
wherein each area is in the form of one or more straight columns or rows constructed of the respective portion of magnetic field sensor elements.

3. The system according to claim 2, wherein at least one of the areas is in the form of at least two straight columns or rows and is constructed of the respective portion of magnetic field sensor elements that are connected in a mesh having more than one dimension.

4. The system according to claim 2, wherein the magnetic field sensor elements of at least two areas are interconnected in a mesh having more than one dimension.

5. The system according to claim 1,
wherein each coil portion is formed by one of the following:
a single wire;
a parallel connection of at least two wires;
at least two wires guided in parallel; and
wherein at least one wire of the respective coil portion is arranged close to each magnetic field sensor element of the respective area.

6. The system according to claim 5,
wherein each area is in the form of one or more straight columns or rows constructed of the respective portion of magnetic field sensor elements and wherein at least one wire of the respective coil portion is arranged close to each column or row, respectively, of the respective area in a straight fashion.

7. The system according to claim 5,
wherein a number of parallel connected wires or parallel guided wires of each coil portion is the same.

8. The system according to claim 1, wherein
a fourth portion of the plurality of magnetic field sensor elements is arranged in a fourth contiguous area, wherein the first, the second, the third and the fourth area are distinct from each other;
the coil wire arrangement comprises a fourth coil portion that is attached serially to the third coil portion; and
the fourth coil portion is arranged close to the sensor elements of the fourth area such that, if the predetermined current is applied to the coil wire arrangement, a fourth magnetic field component is generated at the fourth area having the same orientation as the second magnetic field component;
wherein the magnetic field sensor system is configured to produce a total sensor value that is based on a difference between a sum of the individual sensor values provided within the first and the third area and a sum of the individual sensor values provided within the second and the fourth area.

9. The system according to claim 8, wherein
the third and the fourth area are located between the first and the second area;
the third area is located next to the first area;
the fourth area is located next to the second area; and
the coil portions are arranged in a spiral-like fashion close to the respective areas.

10. The system according to claim 8, wherein the coil portions form a bifilar winding with each two of the coil portions being guided in parallel close to two of the areas that are located neighbouring to each other.

11. The system according to claim 1, which is configured to apply a predetermined calibration current to the coil wire arrangement, and wherein the total sensor value produced during application of the calibration current corresponds to a calibration value.

12. The system according to claim 11, further comprising a further plurality of magnetic field sensor elements, which each are configured to provide an individual sensor value in response to a magnetic field applied thereto and which are electrically interconnected, wherein the magnetic field sensor system is configured to produce a measurement value on the basis of the individual sensor values of the further plurality of magnetic field sensor elements and the calibration value.

13. The system according to claim 12, wherein the measurement value corresponds to an external magnetic field component.

14. The system according to claim 1, further configured to produce a measurement value that is based on a sum of the individual sensor values provided within the first area, the individual sensor values provided within the second area and the individual sensor values provided within the third area.

15. The system according to claim 1, wherein all of the magnetic field sensor elements are of the same sensor type, which is selected from one of the following:
a Hall sensor;
a giant magnetoresistive element;
an anisotropic magnetoresistive element;
a tunnel magnetoresistive element.

16. A magnetic field sensor system, comprising
a plurality of magnetic field sensor elements, which each are configured to provide an individual sensor value in response to a magnetic field applied thereto, and of which a first portion is arranged in a first contiguous area and a second portion is arranged in a second contiguous area being distinct from the first contiguous area, wherein the first and the second contiguous area each are in the form of at least two straight columns or rows and are constructed of the respective portion of magnetic field sensor elements that are connected in a mesh having more than one dimension; and
a coil wire arrangement comprising a first coil portion and a second coil portion being connected in series to the first coil portion, wherein the first coil portion is arranged close to the sensor elements of the first area and the second coil portion is arranged close to the sensor elements of the second area such that, if a predetermined current is applied to the coil wire arrangement, a first magnetic field component is generated at the first area and a second magnetic field component is generated at the second area being opposite to the first magnetic field component;
wherein the magnetic field sensor system is configured to produce a total sensor value that is based on a difference between the individual sensor values provided within the first area and the individual sensor values provided within the second area.

17. The system according to claim 16, wherein the magnetic field sensor elements of the first area are interconnected to the magnetic field sensor elements of the second area in a mesh having more than one dimension.

18. The system according to claim 16,
which is configured to apply a predetermined calibration current to the coil wire arrangement, and wherein the total sensor value produced during application of the calibration current corresponds to a calibration value.

19. The system according to claim 18,
further comprising a further plurality of magnetic field sensor elements, which each are configured to provide an individual sensor value in response to a magnetic field applied thereto and which are electrically interconnected, wherein the magnetic field sensor system is configured to produce a measurement value on the basis of the individual sensor values of the further plurality of magnetic field sensor elements and the calibration value.

20. The system according to claim 16,
further configured to produce a measurement value that is based on a sum of the individual sensor values provided within the first area and the individual sensor values provided within the second area.

\* \* \* \* \*